US009519841B2

(12) United States Patent
Sawaki et al.

(10) Patent No.: US 9,519,841 B2
(45) Date of Patent: Dec. 13, 2016

(54) ATTACHED MATTER DETECTOR AND VEHICLE EQUIPMENT CONTROL APPARATUS

(71) Applicants: Taroh Sawaki, Yokohama (JP); Hideaki Hirai, Yokohama (JP); Ryosuke Kasahara, Yokohama (JP); Hiroyoshi Sekiguchi, Yokohama (JP)

(72) Inventors: Taroh Sawaki, Yokohama (JP); Hideaki Hirai, Yokohama (JP); Ryosuke Kasahara, Yokohama (JP); Hiroyoshi Sekiguchi, Yokohama (JP)

(73) Assignee: RICOH COMPANY, LTD., Tokyo (JP)

( * ) Notice: Subject to any disclaimer, the term of this patent is extended or adjusted under 35 U.S.C. 154(b) by 323 days.

(21) Appl. No.: 14/349,926

(22) PCT Filed: Nov. 1, 2012

(86) PCT No.: PCT/JP2012/078902
§ 371 (c)(1),
(2) Date: Apr. 4, 2014

(87) PCT Pub. No.: WO2013/065868
PCT Pub. Date: May 10, 2013

(65) Prior Publication Data
US 2014/0270532 A1  Sep. 18, 2014

(30) Foreign Application Priority Data

Nov. 2, 2011 (JP) .................................. 2011-241519
Jun. 28, 2012 (JP) .................................. 2012-145674

(51) Int. Cl.
*G06K 9/62* (2006.01)
*G01N 21/43* (2006.01)
(Continued)

(52) U.S. Cl.
CPC ............. *G06K 9/6217* (2013.01); *B60Q 1/143* (2013.01); *G01N 21/43* (2013.01);
(Continued)

(58) Field of Classification Search
None
See application file for complete search history.

(56) References Cited

U.S. PATENT DOCUMENTS

2003/0069674 A1   4/2003  Stam et al.
2005/0035926 A1   2/2005  Takenaga et al.
(Continued)

FOREIGN PATENT DOCUMENTS

CN      1277120 A      12/2000
CN      1834577 A       9/2006
(Continued)

OTHER PUBLICATIONS

Extended European Search Report issued Sep. 14, 2015 in Patent Application No. 12844829.7.
(Continued)

*Primary Examiner* — Chan Park
*Assistant Examiner* — Elisa Rice
(74) *Attorney, Agent, or Firm* — Oblon, McClelland, Maier & Neustadt, L.L.P.

(57) ABSTRACT

An attached matter detector includes a light source configured to irradiate light toward a plate-like transparent member from one surface thereof, an imaging device configured to image reflection light by attached matter on a surface of the plate-like transparent member, a memory configured to previously store flare information obtained by the image device by turning on the light source in a state without having disturbance light and the attached matter on the surface of the plate-like transparent member, and a difference information-obtaining device configured to obtain dif-
(Continued)

ference information between a light-up image as an image obtained by the imaging device with the turned-on light source and a light-out image as an image obtained by the imaging device with the turned-off light source, wherein the attached matter on the surface of the plate-like transparent member is detected based on the difference information and the flare information stored in the memory.

10 Claims, 10 Drawing Sheets

(51) Int. Cl.
    *B60Q 1/14*     (2006.01)
    *G06K 9/78*     (2006.01)
    *G06K 9/00*     (2006.01)
    *G06K 9/20*     (2006.01)
    *B60S 1/08*     (2006.01)

(52) U.S. Cl.
    CPC ......... *G06K 9/00791* (2013.01); *G06K 9/209* (2013.01); *G06K 9/78* (2013.01); *B60Q 2300/41* (2013.01); *B60Q 2300/42* (2013.01); *B60S 1/0844* (2013.01); *B60S 1/0862* (2013.01)

(56) References Cited

U.S. PATENT DOCUMENTS

| | | |
|---|---|---|
| 2006/0163458 A1 | 7/2006 | Reime |
| 2006/0207818 A1 | 9/2006 | Fujioka et al. |
| 2006/0243894 A1 | 11/2006 | Takenaga et al. |
| 2008/0204691 A1* | 8/2008 | Orishimo ............ G03F 7/70533 355/67 |
| 2010/0208060 A1 | 8/2010 | Kobayashi et al. |
| 2010/0208978 A1 | 8/2010 | Terasawa et al. |
| 2011/0031921 A1 | 2/2011 | Han |
| 2013/0039544 A1 | 2/2013 | Robert et al. |

FOREIGN PATENT DOCUMENTS

| | | |
|---|---|---|
| CN | 201166790 Y | 12/2008 |
| CN | 102015384 A | 4/2011 |
| EP | 1 507 138 A2 | 2/2005 |
| JP | 2005-195566 | 7/2005 |
| JP | 2005-195569 | 7/2005 |
| JP | 2006-308329 | 11/2006 |
| JP | 2010-192634 | 9/2010 |
| JP | 2010-204059 | 9/2010 |
| JP | 2010-210607 | 9/2010 |
| WO | WO 2011/107116 A1 | 9/2011 |

OTHER PUBLICATIONS

Combined Office Action and Search Report issued Jun. 3, 2015 in Chinese Patent Application No. 201280053498.7 (with English language translation).

International Search Report issued on Jan. 29, 2013 in PCT/JP2012/078902 filed on Nov. 1, 2012.

* cited by examiner

ATTACHED MATTER DETECTOR AND VEHICLE EQUIPMENT CONTROL APPARATUS

TECHNICAL FIELD

The present invention relates to an attached matter detector which images attached matter such as a raindrop attached on a plate-like transparent member such as a windshield, and detects the attached matter based on the image, and a vehicle equipment control apparatus using the attached matter detector.

BACKGROUND ART

An attached matter detector, which irradiates a plate-like transparent member such as a windshield of a vehicle by a light source, images the reflection light from the plate-like transparent member through an optical filter transmitting the wavelength of the light irradiated from the light source by an imaging element, and detects attached matter such as a raindrop attached on the surface of the plate-like transparent member, is described in Patent Document 1 (Japanese Patent Application Publication No. 2005-195566).

By providing such an optical filter, the attached matter on the plate-like transparent member can be detected without being affected by disturbance light such as sunlight or peripheral light.

However, in the attached matter detector described in Patent Document 1, disturbance light having a wavelength which is the same as that of the light emitted from the light source transmits through the optical filter, so that the disturbance light is false-detected as attached matter. An attached matter detector, which images a light-out image when a light source is turned off and a light-up image when a light source is turned on, calculates a brightness difference between the light-out and light-up images, and detects attached matter such as a raindrop if the brightness difference exceeds a threshold, is described in Patent Document 2 (Japanese Patent Application Publication No. 2005-195569). As described above, by calculating the brightness difference between the light-out and light-up images, disturbance light is eliminated, so that the reflection light component from the light source can be extracted. In this way, the attached matter can be effectively detected.

However, in the above attached matter detector, so-called flare light reflected from a housing of a device may enter into the imaging element when the imaging is performed with the turned-on light source. For this reason, the flare light remains in the difference information between the light-out and light-up images as noise in addition to the light reflected by attached matter. As a result, the attached matter having a brightness value which is approximately the same as that of the flare light is buried in the noise, and can not be detected. Therefore, sufficient detection accuracy can not be obtained.

SUMMARY OF INVENTION

The present invention has been made in view of the above problems, and an object of the present invention is to provide an attached matter detector which can accurately detect attached matter on a plate-like transparent member, and a vehicle equipment control apparatus using the attached matter detector.

To attain the above object, one embodiment of the present invention provides an attached matter detector, including: a light source configured to irradiate light toward a plate-like transparent member from one surface thereof; an imaging device configured to image reflection light by attached matter on a surface of the plate-like transparent member; a memory configured to previously store flare information obtained by the image device by turning on the light source in a state without having disturbance light and the attached matter on the surface of the plate-like transparent member; and a difference information-obtaining device configured to obtain difference information between a light-up image as an image obtained by the imaging device with the turned-on light source and a light-out image as an image obtained by the imaging device with the turned-off light source, wherein the attached matter on the surface of the plate-like transparent member is detected based on the difference information and the flare information stored in the memory.

BRIEF DESCRIPTION OF THE DRAWINGS

The accompanying drawings are included to provide further understanding of the invention, and are incorporated in and constitute a part of this specification. The drawings illustrate an embodiment of the invention and, together with the specification, serve to explain the principle of the invention.

DESCRIPTION OF EMBODIMENT

Figure 1:
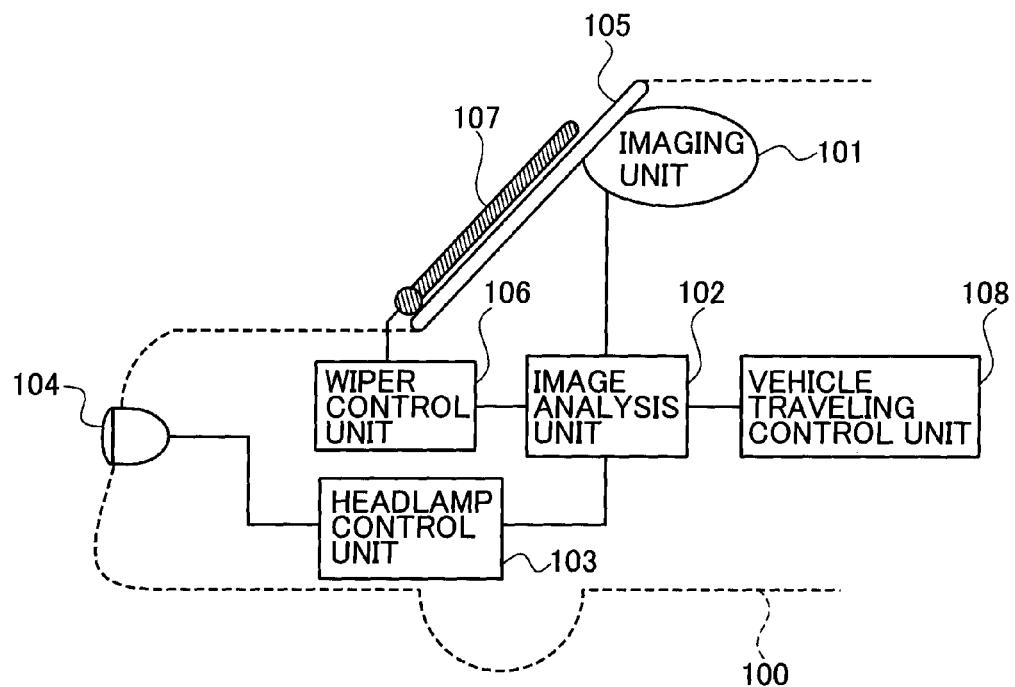
FIG. 1 is a view illustrating a frame format of a vehicle equipment control system in an embodiment.

FIG. 1 is a schematic view illustrating the frame format of the vehicle equipment control system as a vehicle equipment control apparatus in the present embodiment.

The vehicle equipment control system is configured to perform light distribution control of a headlamp, drive control of a wiper and control of other vehicle equipments by using the image data of an area anterior to a vehicle (imaging area) in the traveling direction, which is imaged by an imaging device provided in a vehicle 100 such as an automobile.

The imaging device provided in the vehicle equipment control system of the present embodiment is provided in an imaging unit 101, and is configured to image an area anterior to the vehicle 100 in the traveling direction as the imaging area. The imaging device is provided near a not shown room mirror of a windshield 105 of the vehicle 100, for example. The image data imaged by the imaging device of the imaging unit 101 is input to an image analysis unit 102. The image analysis unit 102 is configured to analyze the image data sent from the imaging device, calculate the position, direction and distance of another vehicle in front of the vehicle 100, detect attached matter such as a raindrop or foreign matter attached on the windshield 105, and also detects a target to be detected such as a white line (compartment line) on a road located in the imaging area. In the detection of another vehicle, a preceding vehicle traveling in the direction which is the same as that of the vehicle 100 is detected by distinguishing a tail lamp of another vehicle, and an oncoming vehicle traveling in the direction opposite to that of the vehicle 100 is detected by distinguishing a headlamp of another vehicle. An attached matter detector includes the imaging unit 101 and the image analysis unit 102 of the present embodiment.

The calculation result of the image analysis unit 102 is sent to a headlamp control unit 103 as a lamp controller. The headlamp control unit 103 is configured to generate a control signal which controls a headlamp 104 as a vehicle equipment of the vehicle 100 based on the distance data calculated by the image analysis unit 102. More specifically, the headlamp controller 103 is configured to control the switching of the full beam and dipped beam of the headlamp 104 and the partial shielding of the light of the headlamp 104, so as to ensure the eyesight of a driver of the vehicle 100 while preventing dazzling of a driver of another vehicle by avoiding the entrance of the strong light of the headlamp 104 of the vehicle 100 into the eyes of a driver of a preceding vehicle or oncoming vehicle.

The calculation result of the image analysis unit 102 is also sent to a wiper control unit 106 as a wiper controller. The wiper control unit 106 is configured to eliminate attached matter such as a raindrop or foreign matter attached on the windshield 105 of the vehicle 100 by controlling the wiper 107. The wiper control unit 106 is configured to receive the detection result of the foreign matter by the image analysis unit 102, and generate the control signal which controls the wiper 107. If the control signal generated by the wiper control unit 106 is sent to the wiper 107, the wiper 107 is operated to ensure the eyesight of the driver of the vehicle 100.

The calculation result of the image analysis unit 102 is also sent to a vehicle traveling control unit 108 as a vehicle traveling controller. The vehicle traveling control unit 108 is configured to perform traveling support control, which notifies the driver by the alarm of the vehicle 100, and controls the steering wheel or brakes of the vehicle when the vehicle 100 is deviated from a traffic lane zoned by a while line, based on the detection result of the white line detected by the image analysis unit 102.

Figure 2:
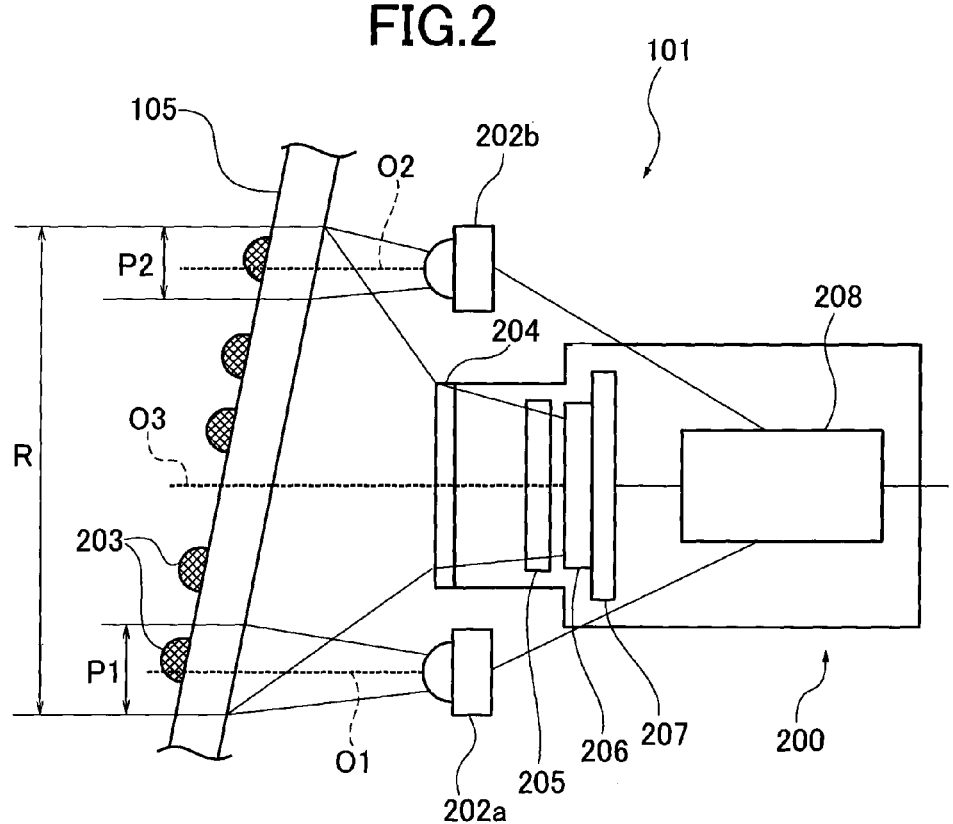
FIG. 2 is a schematic view illustrating an imaging unit 101.

FIG. 2 is a schematic view illustrating the imaging unit 101.

The imaging unit 101 includes an imaging device 200 and two light sources 202a, 202b. The imaging unit 101 is disposed on the inner wall surface side of the windshield 105 of the vehicle 100. The imaging device 200 includes an imaging lens 204, optical finder 205, sensor substrate 207 having an imaging element 206, and signal processor 208. The signal processor 208 is an image processor such as a CPU or DSP, and is configured to generate image data in which analogue electric signals (the light volume received by each light-receiving element on the imaging element 206) output from the sensor substrate 207 are converted into digital electric signals. The signal processor 208 is configured to control an exposure time of the imaging element 206.

The two light sources 202a, 202b are disposed near the imaging device 200. The respective light sources 202a, 202b are disposed such that their optical axes O1, O2 are approximately parallel to the optical axis O3 of the imaging lens 204, and the angle of view range R of the imaging lens 204 overlaps with the irradiation areas P1, P2 of the light sources 202a, 202b on the windshield 105. The respective light sources 202a, 202b are connected to the signal processor 208, and the signal processor 208 is configured to control the turning on and off of the respective light sources 202a, 202b.

The light from the subject (detection object) in the angle of view range R of the imaging lens 204 passes through the imaging lens 204, transmits through the optical filter 205, and is converted into electric signals according to the light intensity in the imaging element 206. If the electric signals (analogue signals) output from the imaging element 206 are input to the signal processor 208, the digital signals showing the brightness of each pixel on the imaging element 206 are output from the electric signals as image data. In this case, attached matter such as a raindrop on a windshield and a landscape in front of the vehicle is the subject (detection object).

The focal position of the imaging lens 204 is set in infinity or between infinity and the windshield 105. In this way, appropriate information can be obtained from the image data of the imaging device 200 not only when detecting a raindrop 203 attached on the windshield 105 but also when detecting a white line or detecting a preceding vehicle or oncoming vehicle.

When detecting the raindrop 203 attached on the windshield 105, a shape recognition process, which determines whether or not a raindrop candidate image on the image data has a circular shape by the image analysis unit 102, and identifies the raindrop candidate image as the raindrop image, is performed because many of the raindrop images on the imaging data have a circular shape. When performing the shape recognition process, it is preferable for the imaging lens 204 to be focused on infinity or between infinity and the windshield 105 as described above, not the raindrop 203 on the outer wall surface of the windshield 105, in order to obtain an out-of-focus raindrop image. With this constitution, the shape recognition rate (circular shape) of the raindrop is increased, and the raindrop detection performance is improved.

Figure 3:
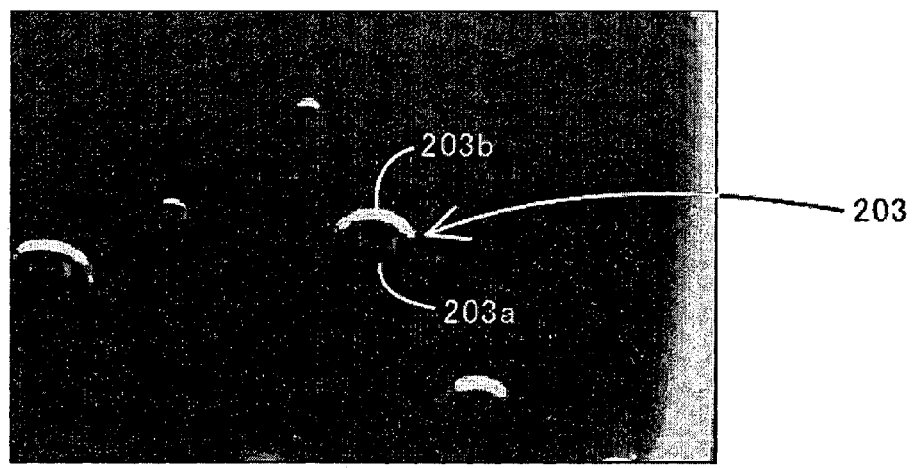
FIG. 3 is a view illustrating infrared light image data for detecting a raindrop when an imaging lens is focused on a raindrop on an outer wall surface of a windshield of a vehicle.

FIG. 3 is a view illustrating infrared light image data for detecting a raindrop when the imaging lens 204 is focused on the raindrop 203 on the outer wall surface of the windshield 105.

Figure 4:
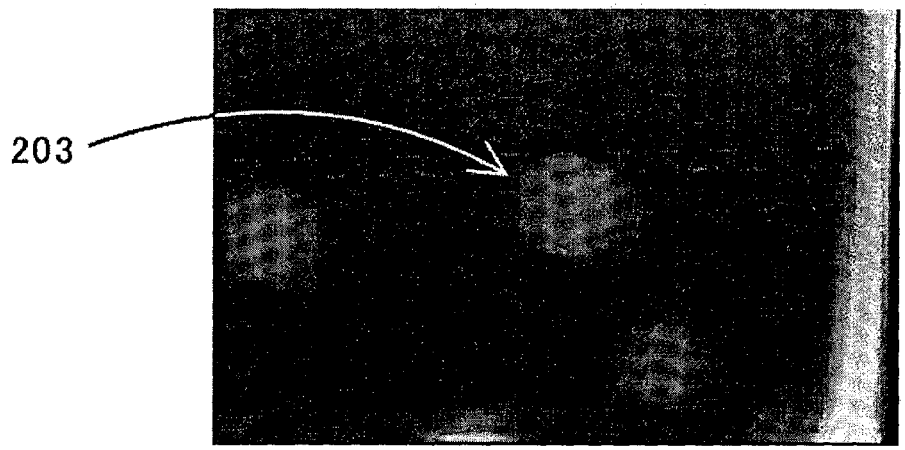
FIG. 4 is a view illustrating infrared light image data for detecting a raindrop when the imaging lens is focused on infinity.

FIG. 4 is a view illustrating infrared light image data for detecting a raindrop when the imaging lens 204 is focused on infinity.

When the imaging lens 204 is focused on the raindrop 203 on the outer wall surface of the windshield 105, the image of the raindrop 203 in which a background image 203a appears is imaged as illustrated in FIG. 3. Such a background image 203a causes the false-detection of the raindrop 203. The brightness of a part of the raindrop 203b may be increased to form an arch shape, for example, as illustrated in FIG. 3, and the shape of the large brightness portion, i.e., the shape of the raindrop image is changed according to the direction of sunlight or the position of a street lamp. By addressing the changeable raindrop image shape with the shape recognition process, the process load of the shape recognition process is increased, and the recognition accuracy is deteriorated.

On the other hand, when the imaging lens 204 is focused on infinity, an out-of-focus image is generated as illustrated in FIG. 4. Therefore, the appearing of the background image 203a is not reflected on the image data, and the false-detection of the raindrop 203 can be reduced. A change in the shape of the raindrop image due to the direction of sunlight and the position of a street lamp is reduced by the generation of the out-of-focus image, so that the shape of the raindrop always becomes an approximately circular shape. Thus, the load of the shape recognition process of the raindrop 203 is reduced, and the recognition accuracy is improved.

When distinguishing the tail lamp of the preceding vehicle traveling a distance, if the imaging lens is focused on infinity, the number of light-receiving elements which receive the light of the tail lamp on the imaging element 206 may be about one. In this case, the light of the tail lamp may not be received by the light-receiving element for red which receives the color (red) of the tail lamp. In this case, the tail lamp can not be recognized, and the preceding vehicle can not be detected. In order to avoid such a failure, it is preferable for the imaging lens 204 to be focused before infinity. In this way, the tail lamp of the preceding vehicle traveling a distance is out-of-focused, so that the number of light-receiving elements which receive the light of the tail lamp can be increased. Consequently, the recognition accuracy of the tail lamp is increased, and thus, the detection accuracy of the preceding vehicle can be improved.

A light-emitting diode (LED), semiconductor laser (LD) or the like can be used for the light sources 202a, 202b of the imaging unit 101. For example, visible light or infrared light can be used for the emission wavelength of the light source 202. However, it is preferable to select the wavelength which is longer than that of the visible light and is covered by the light-receiving sensitivity of the imaging element 206, for example, the wavelength of infrared light area of 800 nm or more and 1000 nm or less, in order to avoid the dazzling of a driver of an oncoming vehicle or pedestrian due to the light of the light source. The light source 202 of the present embodiment is configured to irradiate light having a wavelength of an infrared light area.

When imaging the infrared wavelength light from the light source 202 reflected by the windshield 105 with the imaging device 200, the imaging element 206 of the imaging device 200 receives not only the infrared wavelength light from each light source 202a, 202b but also a large volume of disturbance light including infrared wavelength light such as sunlight. In order to distinguish the infrared wavelength light from each light source 202a, 202b from a large volume of the disturbance light, it is necessary to sufficiently increase the emission amount of each light source 202a, 202b to be sufficiently larger than that of the disturbance light. However, it is difficult to use such a light source which emits a large volume of light.

In this embodiment, the light from each light source 202a, 202b is received by the imaging element 206 through the optical filter 205. As the optical filter 205, a cut filter which cuts light having a wavelength shorter than the emission wavelength of each light source 202a, 202b, or a band pass filter in which the peak of transmittance approximately conforms to the emission wavelength of each light source 202a, 202b can be used. By receiving the light from each light source 202a, 202b with the imaging element 206 through the optical filter 205, the light can be received after eliminating the light except the emission wavelength of the light source 202a, 202b, so that the light volume from each light source 202a, 202b which is received by the imaging element 206 is increased relative to the disturbance light. As a result, the light from each light source 202a, 202b can be distinguished from the disturbance light even if the light source does not emit a large volume of light.

However, in the present embodiment, the raindrop 203 on the windshield 105 is detected from the imaging data, and a preceding or oncoming vehicle is also detected and also a white line is detected from the imaging data. For this reason, if the wavelength range except the infrared wavelength light that each light source 202a, 202b irradiates is eliminated from the entire image, the light of the wavelength range necessary for the detection of a preceding vehicle and oncoming vehicle and the detection of a white line can not be received by the imaging element 206, so that the detection is affected. In the present embodiment, a filter, which divides the image area of the image data into an image area for detecting the raindrop 203 on the windshield 105 and an image area for detecting a preceding vehicle or oncoming vehicle and detecting a white line, and eliminates the wavelength range except the infrared wavelength light that the each light source 202a, 202b irradiates only in the portion corresponding to the image area for detecting a raindrop, is provided as the optical filter 205.

Figure 5:
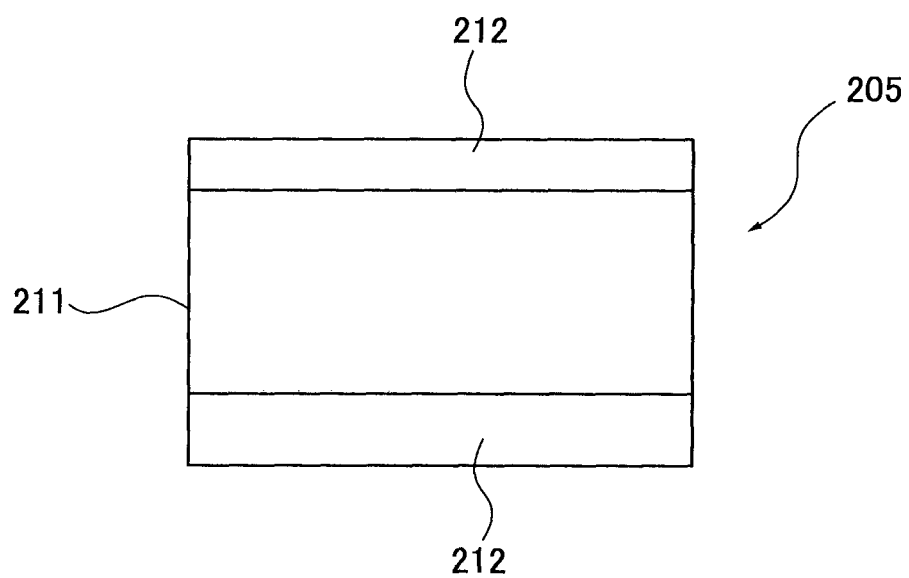
FIG. 5 is a front view illustrating an optical filter of an imaging device.

FIG. 5 is a front view illustrating the optical filter 205.

As illustrated in FIG. 2, the illuminations areas P1, P2 of the light sources 202a, 202b are located in the upper and lower portions of the angle of view range R of the imaging lens 204, respectively. Each of the upper portion (¼) and lower portion (¼) of the image becomes the image area for detecting a raindrop as an attached matter imaging area which detects foreign matter or a raindrop on the windshield 105, and the center portion (½) of the screen becomes the image area for detecting a vehicle which detects a preceding vehicle, oncoming vehicle, road surface area or white line. Therefore, the optical filter 205 includes in a portion corresponding to the lower portion (¼) of the image and a portion corresponding to the upper portion (¼) of the image, which are the image areas for detecting a raindrop, an infrared light transmittance filter area 212 which eliminates the wavelength range except the infrared wavelength light that the light source 202 irradiates.

The images of the headlamp of the oncoming vehicle, the tail lamp of the preceding vehicle and the white line are mostly found in the central portion of the image, and the image of the road in front of the vehicle is normally found in the lower portion of the image. The upper portion of the image normally includes a sky image. Accordingly, in the light distribution control and the vehicle control, the information in the central portion of the image screen is important and the information of the upper and lower portions of the image screen is not very important. When detecting both of the oncoming vehicle, preceding vehicle or white line and the raindrop from single image data, as illustrated in FIG. 2, it is preferable to provide the irradiation areas P1, P2 of the light sources 202a, 202b in the upper and lower portions of the angle of view range R of the imaging lens 204, and set the upper and lower portions of the image as the image area for detecting a raindrop and to set the remaining central portion of the image as the image area for detecting a vehicle.

The lower portion of the image area may include a bonnet of a vehicle if the imaging direction of the imaging device 200 is inclined downwardly. In this case, the sunlight reflected by the bonnet of the vehicle and the tail lamp of the preceding vehicle become the disturbance light, and this disturbance light is included in the image data, causing the false-detection of the headlamp of the oncoming vehicle, the tail lamp of the preceding vehicle and the white line. However, in the present embodiment, a filter (cut filter or band pass filter) which eliminates a wavelength range except infrared wavelength light that the light source 202 irradiates is provided in the portion corresponding to the lower portion of the image, so that the disturbance light such as the sunlight reflected by the bonnet or the tail lamp of the preceding vehicle is eliminated. Consequently, the accuracy for distinguishing the headlamp of the oncoming vehicle, the tail lamp of the preceding vehicle and the white line can be improved.

The disturbance light may include the wavelength which is the same as the infrared wavelength that the light source 202 irradiates. Such disturbance light transmits through the infrared light transmittance filter area 212 of the optical filter 205. For example, the infrared wavelength component in the sunlight transmits through the infrared light transmittance filter area 212 of the optical filter 205 in the daytime. The infrared wavelength component in the headlight of the oncoming vehicle transmits through the infrared light transmittance filter area 212 of the optical filter 205 in the nighttime. The disturbance light may be false-detected as a raindrop because the disturbance light transmits through the infrared light transmission filter area 212 as described above. If the image process for detecting a raindrop includes an algorithm which determines a raindrop by a constant brightness value or more, the brightness value becomes a constant value or more due to the disturbance light although the raindrop is not actually found, and the raindrop is determined.

In this embodiment, in order to prevent the above-described false-detection, the imaging unit 101 turns on each light source 202a, 202b, and images the light-up image. Next, the imaging unit 101 turns off each light source 202a 202b, and images the light-out image. Then, the image analysis unit 102 obtains the difference image between the light-up image and the light-out image, and detects a raindrop based on the difference image obtained as the difference information. In this embodiment, the image analysis unit 102 has an operation as a difference information-obtaining device. More specifically, the image analysis unit 102 controls each light source 202a, 202b electrically connected to the signal processor 208 while synchronizing the turning-on of each light source 202a, 202b with the exposure timing of the imaging element 206. Namely, each light source 202a, 202b is turned on while synchronizing with the exposure timing of the imaging element 206, and the light-up image is imaged. Then, each light source 202a, 202b is turned off while synchronizing with the next exposure timing of the imaging element 206, and the light-out image is imaged. Moreover, each light source 202a, 202b is always turned off except for a time of imaging a light-up image for detecting a raindrop. Consequently, the power consumption can be reduced.

The brightness value Ya of the light-up image data photographed by turning on each light source 202a, 202b, which is output from the signal processor 208, includes both of reflection light from a raindrop and disturbance light. The brightness value Yb of the light-out image data photographed by turning off each light source 202a, 202b, which is output from the signal processor 208, includes only disturbance light. In this case, the image analysis unit 102 as the difference information-obtaining device calculates Yr=Ya−Yb regarding each pixel in the image area for detecting a raindrop, and generates the difference image data as difference information. The brightness value Yr of the difference image data is a value in which the light obtained by the reflection light from a raindrop after eliminating only the effect of the disturbance light is only detected.

Figure 6C:
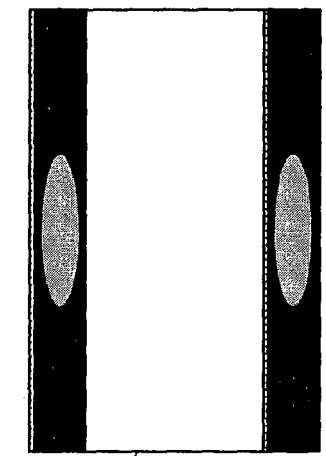
FIGS. 6A, 6B, 6C are views illustrating examples of a light-out image, light-up image and difference image without disturbance light.
Figure 6B:
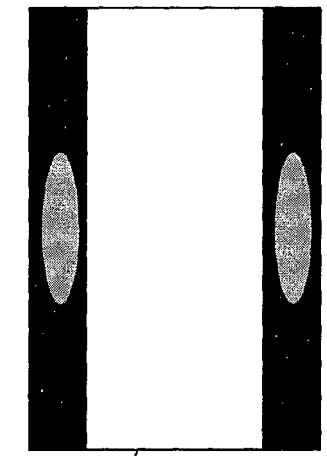
Figure 6A:
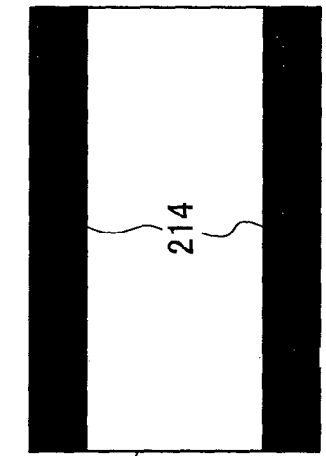

FIG. 6A is a view illustrating a light-out image without disturbance light. FIG. 6B is a view illustrating a light-up image without disturbance light. FIG. 6C is a view illustrating a difference image between the light-up image and the light-out image without disturbance light.

As illustrated in FIG. 6A, each image area 214 for detecting a raindrop of the light-out image without disturbance light has no light, each image area 214 for detecting a raindrop is black, and the brightness value becomes 0. On the other hand, as illustrated in FIG. 6B, a part of the image area 214 for detecting a raindrop, which corresponds to the portion where the reflection light from the light source reflected by a raindrop enters in the imaging element 206, is slightly increased in light. In this case, as illustrated in FIG. 6C, the difference image becomes an image which is the same as that of the light-up image illustrated in FIG. 6B.

Figure 7C:
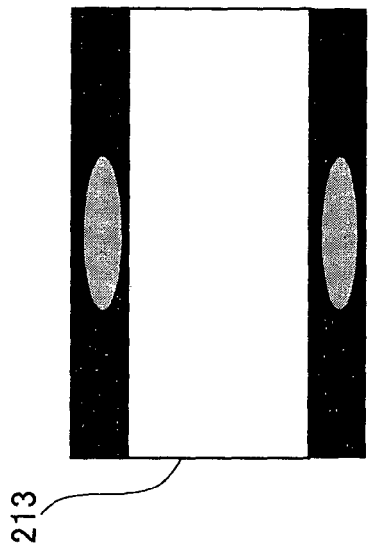
FIGS. 7A, 7B, 7C are views illustrating examples of a light-out image, light-up image and difference image with disturbance light.
Figure 7B:
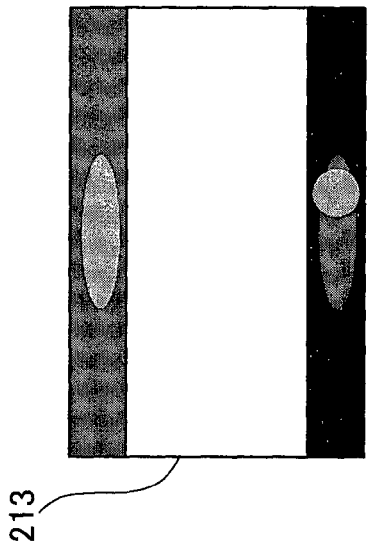
Figure 7A:
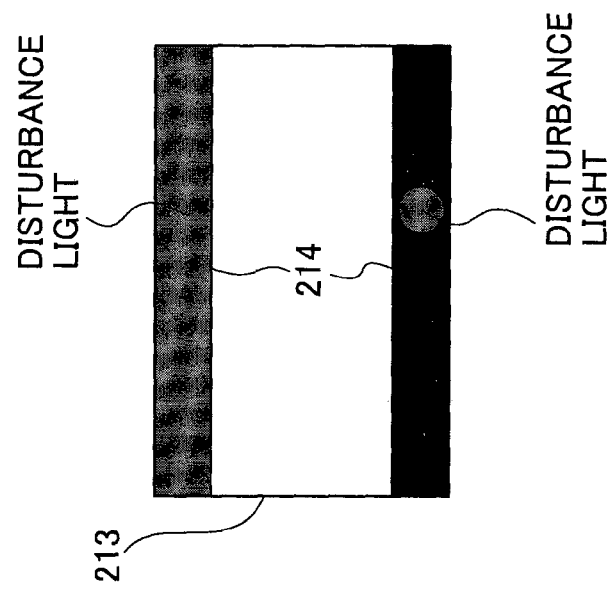

FIG. 7A is a view illustrating a light-out image with disturbance light. FIG. 7B is a view illustrating a light-up image with disturbance light. FIG. 7C is a view illustrating a difference image between the light-up image and the light-out image with disturbance light.

As illustrated in FIG. 7A, a part of the image area 214 for detecting a raindrop in the light-out image with disturbance light, which corresponds to the portion where the disturbance light enters in the imaging element 206 is slightly increased in light. In the example illustrated in FIG. 7A, the entire area of the image area 214 for detecting a raindrop in the upper portion of the light-out image is slightly increased in light by the disturbance light, and a part of the image area 214 for detecting a raindrop in the lower portion of the light-out image is increased in light by the disturbance light.

Next, in the image area 214 for detecting a raindrop in the upper portion of the light-up image as illustrated in FIG. 7B, since the reflection light and the disturbance light enter the portion where the reflection light from the light source reflected by a raindrop enters, that portion is increased in light compared to another portion. In the image area for detecting a raindrop in the lower portion of the light-up image, the portion corresponding the portion of the imaging element 206 where the reflection light from a raindrop only enters is slightly increased in light, and the portion corresponding the portion of the imaging element 206 where the reflection light from a raindrop and the disturbance light enter is increased in light.

Then, by obtaining the difference between the light-up image and the light-out image, as illustrated in FIG. 7C, the difference image becomes an image from which the disturbance light is eliminated.

Among disturbance light, for example, sunlight does not vary over a short time. For this reason, the disturbance light can be accurately eliminated by generating the difference image even if the imaging of the light-up image and the imaging of the light-out image have an interval. However, when the position of the disturbance light varies over a short time by the headlight of an oncoming vehicle during the traveling of a vehicle, the disturbance light can not be accurately eliminated from the generated difference image if the imaging of the light-up image and the imaging the light-out image have an interval. Therefore, it is preferable to continuously image the light-up image and the light-out image.

As described above, by obtaining the difference image between the light-up image and the light-out image, the disturbance light can be preferably eliminated. However, when imaging the light-up image, a part of the reflection light reflected by the windshield 105 may enter the imaging element 206 as flare light. This flare light remains in the difference image as noise. Due to such noise of the flare light, there may be a case that the raindrop candidate image on the difference image data is not distinguished as a circular shape in the shape recognition process. As a result, the shape recognition rate (circular shape) of the raindrop can not be sufficiently increased, and the raindrop detection performance can not be sufficiently improved.

Consequently, in the present embodiment, a flare image is obtained in advance by turning on the light sources 202a, 202b under an environment without having disturbance light and attached matter on a windshield, and the obtained flare image is stored in a memory such as ROM. The image captured by turning on the light sources 202a, 202b under an environment without having disturbance light and attached matter on a windshield is a flare image in which flare light only enters. Thereby, the information of the flare light can be obtained.

Then, the difference image (hereinafter referred to as a second difference image) between the flare image stored in the memory and the difference image (hereinafter referred to as a first difference image) of the light-up image and the light-out image is obtained. Both of the disturbance light and flare light are thereby eliminated, and the image only by the reflection light from the light source reflected by a raindrop can be obtained. By performing the shape recognition process with the data of the second difference image, it can be accurately determined whether or not the raindrop candidate image on the second difference image data is a circular shape. Thus, a raindrop can be highly accurately detected.

Figure 8:
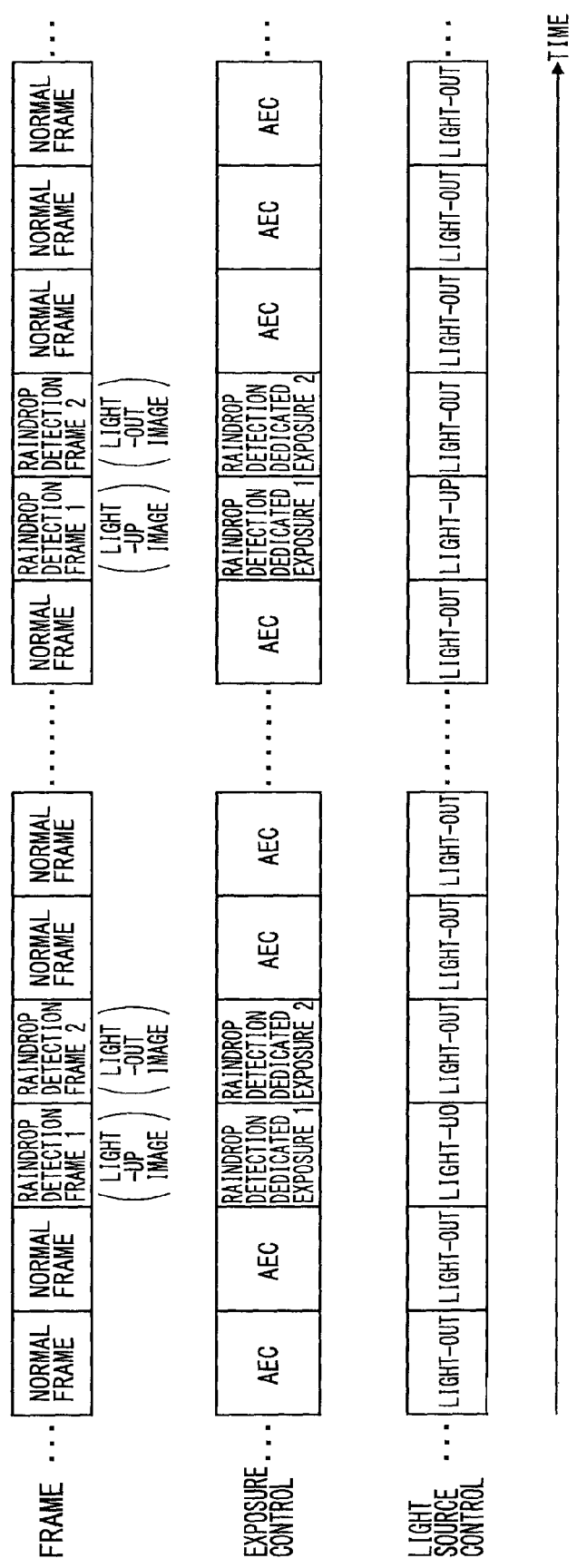
FIG. 8 is a basic imaging sequence view of an imaging unit.

FIG. 8 is the basic image sequence view of the imaging unit 101.

An automatic exposure control (AEC) which stops exposure is performed, and the respective light sources 202a, 202b are turned off if a brightness value of the central portion of a screen reaches a predetermined brightness value in a normal frame which images a normal image for vehicle control and light distribution control with the image area 213 for detecting a vehicle in the central portion of the image. After the imaging of a predetermined number of normal images, a raindrop detection frame 1 which images the light-up image and a raindrop detection frame 2 which images the light-out image are continuously inserted. During these 2 frames, the exposure control is not the automatic exposure control in the normal frame, and is exposure control dedicated for detecting a raindrop. More specifically, the exposure time of the raindrop detection frame 1 and the exposure time of the raindrop detection frame 2 are set to be the same. In the raindrop detection frame 1 which images the light-up image, the respective light sources 202a, 202b are turned on, and in the raindrop detection frame 2 which images the light-out image, the respective light sources 202a, 202b are turned off. In the image analysis unit 102, the first difference image between the light-up image obtained by the raindrop detection frame 1 and the light-out image obtained by the raindrop detection frame 2 is generated. Then, the second difference image between the first difference image and the flare image stored in a memory such as a ROM is generated, and the raindrop detection process is performed based on this second difference image.

The reason for performing the exposure control dedicated for detecting a raindrop, not the automatic exposure control, and setting the same exposure time for each raindrop detection frame is as follows. Namely, the exposure time of the raindrop detection frame 1 may differ from the exposure time of the raindrop detection frame 2 if the automatic exposure control is performed in each raindrop detection frame. The brightness value of disturbance light differs if the exposure time differs, and the disturbance light remains in the difference image, and thus, the raindrop can not be accurately detected. For this reason, in the present embodiment, the exposure control dedicated for detecting a raindrop is conducted, and the exposure time for each raindrop detection frame is set to be the same, so that the brightness value of the disturbance light in the light-up image is set to be approximately the same as that of the disturbance light in the light-out image. Therefore, the first difference image from which most of the disturbance light is eliminated can be generated. Thus, a raindrop can be highly accurately detected.

In the above case, since the automatic exposure control is not performed in each raindrop detection frame, the image of the image area for detecting a vehicle in the central portion of the image is deteriorated, and the images of the headlamp of the oncoming vehicle, the tail lamp of the preceding vehicle and the white line can not be accurately detected, so that the vehicle control and the light distribution control can not be performed in each raindrop detection frame. Moreover, the raindrop detection frames 1, 2 can not be frequently inserted. A method of correcting the light-up image and the light-out image by the exposure time in each imaging, and generating the first difference image from the corrected light-up image and light-out image can be performed. Namely, the brightness value Ya' of each pixel of the corrected light-up image can be expressed as Ya'=Ya/Ta and the brightness value Yb' of each pixel of the corrected light-out image can be expressed as Yb'=Yb/Tb where the exposure time in imaging the light-up image is Ta and the exposure time in imaging the light-out image is Tb. Therefore, the brightness value Yr' of each pixel of the first difference image from the corrected light-up image and the light-out image is expressed as Yr'=Ya'−Yb'. Consequently, the first difference image from which most of disturbance light is eliminated can be generated even if the exposure time in imaging the light-up image differs from the exposure time in imaging the light-out image. Moreover, the automatic exposure control can be performed in each raindrop detection frame, so that the images of the headlamp of the oncoming vehicle, the tail lamp of the preceding vehicle and the white line can be accurately detected even in each raindrop detection frame. Accordingly, the raindrop detection and the detection of the area anterior to a vehicle can be simultaneously conducted.

In the above, the shape recognition process is conducted for the difference image, and the wiper control is performed according to the number of detected raindrops. The raindrop detection can be performed according to the total brightness value by calculating the total brightness value of the second difference image because most of the disturbance light and the flare light can be eliminated in this embodiment. More specifically, the raindrop is determined if the total brightness value in the second difference image reaches a predetermined brightness value or more. The load of the image analysis unit 102 can be thereby reduced. When performing the raindrop detection from the total brightness value in the first difference image data, it is necessary to set a threshold to be a higher value for the noise of the flare light in order to prevent the false-detection due to the noise of the flare light, and the raindrop can not be highly accurately detected. However, in this embodiment, by using the second difference image from which the noise of the flare light is eliminated, the threshold can be set to a lower value, and the raindrop detection accuracy can be improved even in the raindrop detection from the total brightness value.

However, the brightness value of the reflection light from the light source may vary according to the exposure time if the raindrop detection is performed by the automatic exposure control (AEC) when detecting the raindrop from the total brightness value of the second difference image. As a result, the false-detection as a lot of raindrops occurs because the total brightness value is increased if the exposure time is long even with the same amount of rain. Therefore, in the system which detects the raindrop from the total brightness value, the irradiation volume of each light source 202a, 202b is changed in accordance with the exposure time when imaging the light-up image.

More specifically, since the exposure time hardly changes in the previous and next frames, the irradiation light volume of each light source 202a, 202b (voltage value of each light source 202a, 202b) is obtained based on the exposure time of the previous frame which images the light-up image, and the obtained irradiation light volume is irradiated on the windshield 105 in imaging the light-up image. Namely, the exposure time in the automatic exposure control (AEC) when imaging the light-up image is anticipated as the exposure time which is the same as that of the previous frame, and the irradiation light volume of each light source 202a, 202b is obtained. The exposure time in the automatic exposure control (AEC) when imaging the light-up image can be anticipated based on the average of the exposure time of the past frames and the movement average, and the irradiation light volume of each light source 202a, 202b (voltage value of each light source 202a, 202b) can be obtained. The raindrop detection can be thereby performed in the automatic exposure control (AEC), and both of the raindrop detection and the detection of the area anterior to a vehicle can be simultaneously conducted, and the raindrop can be detected from the total brightness value of the image area 214 for detecting a raindrop.

There may be a case that disturbance light greatly differs over a short time. In this case, the disturbance light component of the light-up image significantly differs from the disturbance light component of the light-out image even if the light-up image and the light-out images are continuously imaged. For example, when the light-up image and the light-out image are continuously imaged at the moment when changes in conditions occur from to shadow on a sunny day, the disturbance light component of the light-up image greatly differs from the disturbance light component of the light-out image. As a result, the effect of the disturbance light remains in the first difference image. For this reason, when detecting a raindrop by the shape recognition process, it may not be determined whether or not the raindrop candidate image is a circular shape due to this disturbance light. Moreover, when detecting a raindrop based on the total brightness value in the second difference image, due to the disturbance light, the threshold is exceeded although the raindrop is not attached, so that the raindrop may be false-detected.

Therefore, the light-out image, light-up image and light-out image are continuously imaged in order, and the light-out image just before the light-up image can be compared to the light-out image just after the light-up image, and it can be determined whether or not the raindrop detection is performed.

Hereinafter, the modified example will be described.

Figure 9:
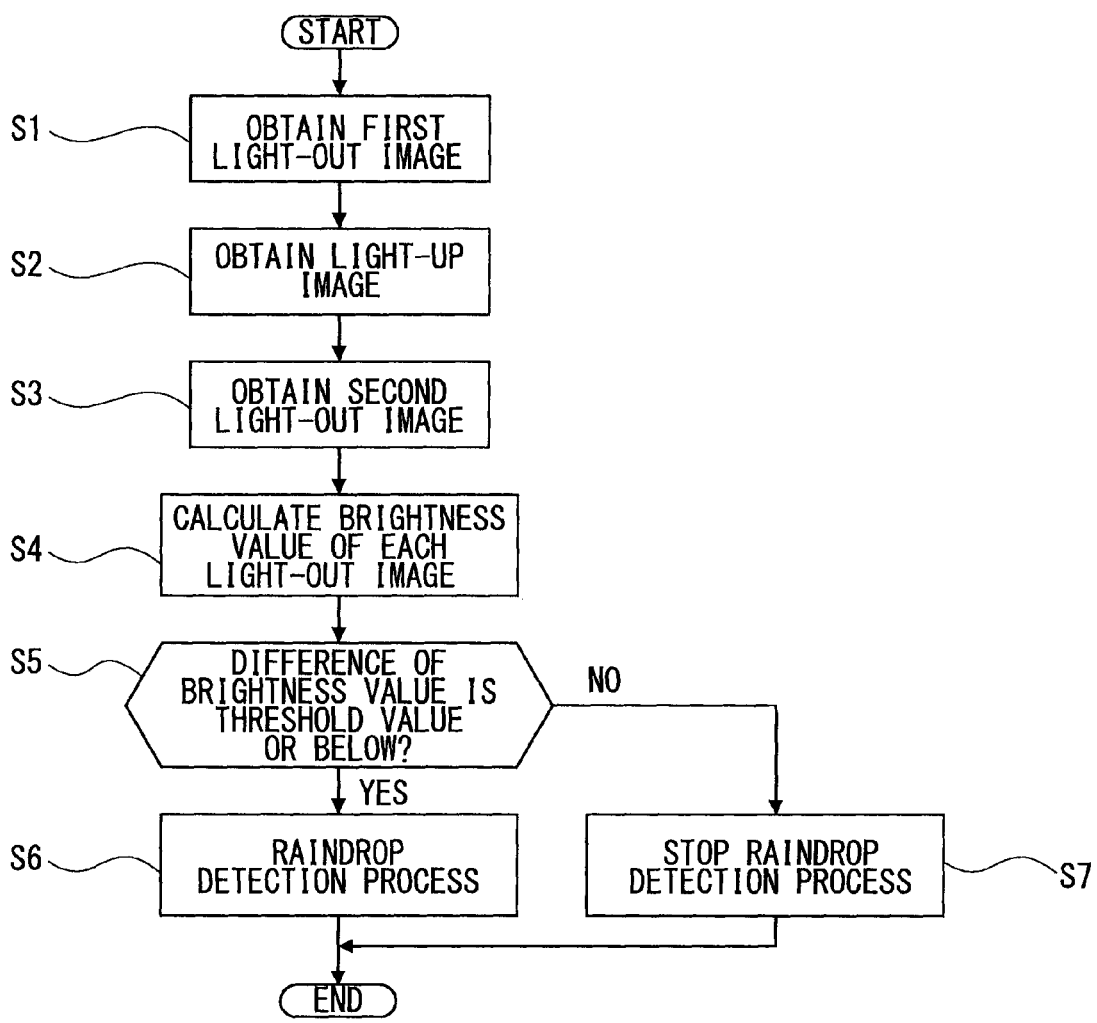
FIG. 9 is a view illustrating a control flow of a process of detecting a raindrop in a modified example.
Figure 10:
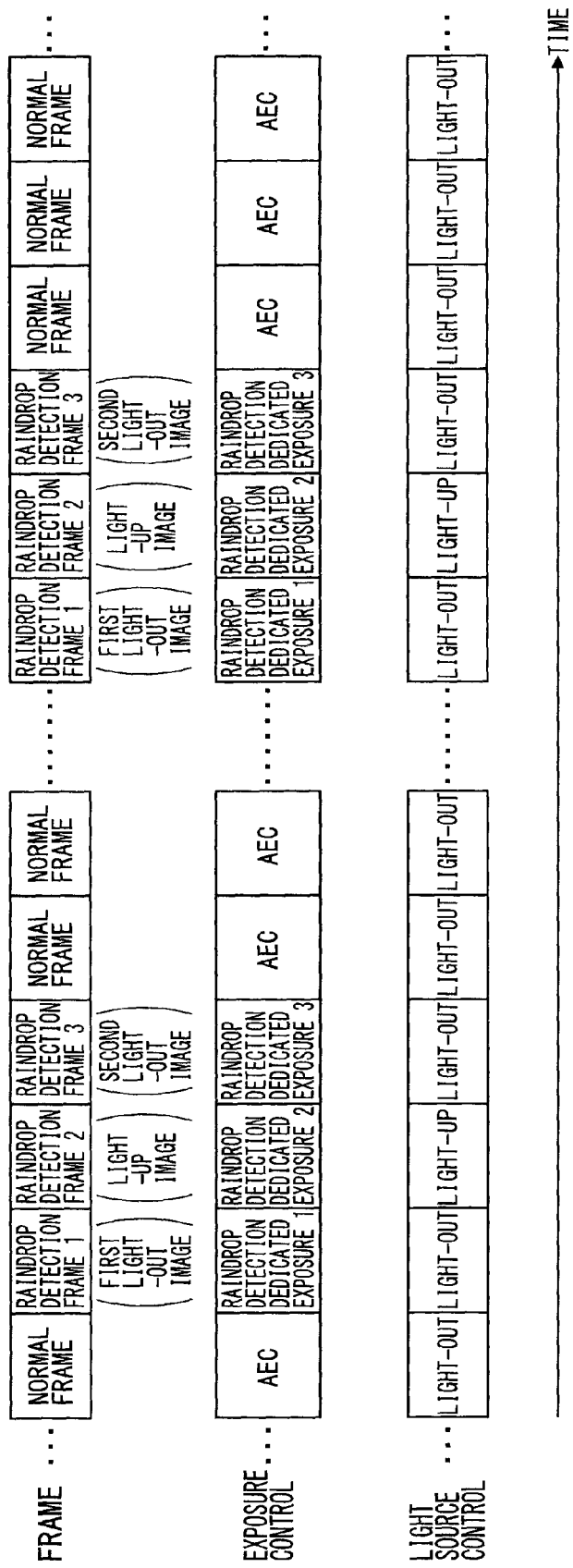
FIG. 10 is an imaging sequence view in a modified example.

FIG. 9 is a view illustrating a control flow of a raindrop detection process in the modified example. FIG. 10 is an imaging sequence view in the modified example.

As illustrated in FIG. 10, after imaging a predetermined number of normal images, a raindrop detection frame 1 which images the first light-out image, a raindrop detection frame 2 which images a light-up image and a raindrop detection frame 3 which images the second light-out image are continuously inserted, and the first light-out image, light-up image and second light-out image are continuously obtained in steps S1-S3 in FIG. 9.

Figure 11:
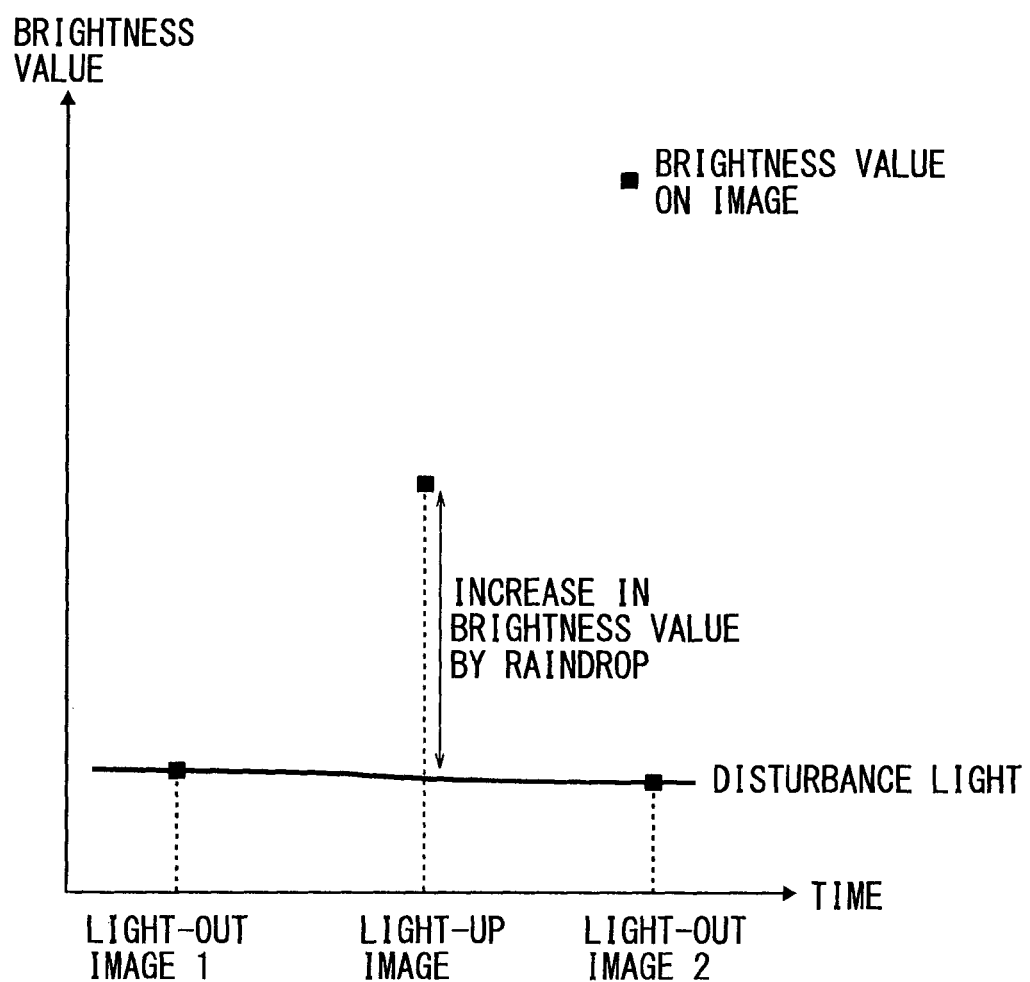
FIG. 11 is a graph illustrating a brightness value when disturbance light is not greatly changed between the light-up image and the light-out image.

Next, the total brightness value of the first light-out image and the total brightness value of the second light-out image are calculated in step S4. Next, the difference value between the total brightness value of the first light-out image and the total brightness value of the second light-out image is calculated, and it is checked whether or not the difference value is a threshold or below in step S5. During a period from the imaging time of the first light-out image and the imaging time of the second light-out image, when the disturbance light is not significantly changed, the brightness values of the disturbance light of the respective images are approximately the same as illustrated in FIG. 11. Therefore, in this case, most of the disturbance light is eliminated from the first difference image between the second light-out image and light-up image. Consequently, if the difference value between the total brightness value of the first light-out image and the total brightness value of the second light-out image is a threshold or below (Yes in step S5), the raindrop detection process is performed in step S6.

Figure 12:
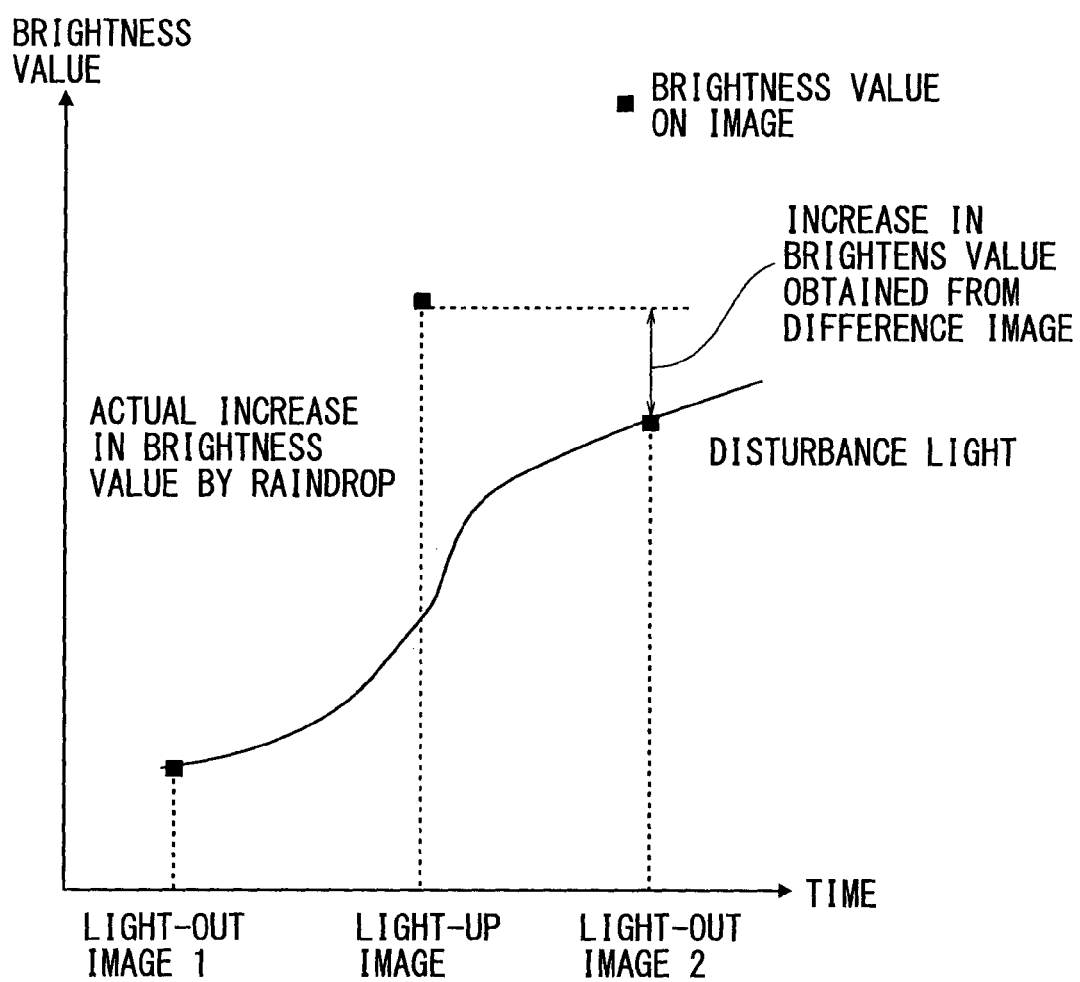
FIG. 12 is a graph illustrating a brightness value when disturbance light is greatly changed between the light-up image and light-out image.

On the other hand, as illustrated in FIG. 12, when the brightness value of the light-up image and the brightness value of the second light-out image greatly change, the brightness value of the first light-out image and the brightness value of the second light-out image greatly change. Therefore, if the difference between the brightness value of the first light-out image and the brightness value of the second light-out image exceeds a threshold (No in step S5), the effect of the disturbance light remains in the first difference image between the second light-out image and the light-up image. As a result, the false-detection may occur due to the effect of the disturbance light. In this case, the raindrop detection process is stopped in Step S7.

In the above, as illustrated in FIG. 10, the exposure control dedicated for detecting a raindrop, not the automatic exposure control, is performed, and the exposure time for the respective raindrop detection frame is set to be the same, but the raindrop detection can be performed by the automatic exposure control (AEC). In this case, the exposure time may differ between the first light-out image and the second light-out image. If the exposure time differs between the two light-out images, the brightness value of any one of the images is corrected by the exposure time. Namely, when correcting the brightness value Y1 of the first light-out image, the brightness value Y1' after correcting the first light-out image is corrected as $Y1'=Y1 \times (E2/E1)$ where the exposure time of the first light-out image is E1 and the exposure time of the second light-out image is E2.

The above description is one example, and the present invention has the following effect with respect to each of the following (1)-(7).

(1) The attached matter detector (the imaging unit 101 and the image analysis unit 012 of the present embodiment)

includes the light source 202*a*, 202*b* configured to irradiate light toward the plate-like transparent member from one surface thereof, the imaging device 200 configured to image the reflection light by attached matter such as the raindrop 203 on the surface of the plate-like transparent member, the memory configured to previously store the flare information obtained by the image device by turning on the light source in a state without having disturbance light and the attached matter on the surface of the plate-like transparent member, and the difference information-obtaining device configured to obtain the difference information between the light-up image as an image obtained by the imaging device with the turned-on light source and the light-out image as an image obtained by the imaging device with the turned-off light source, wherein the attached matter on the surface of the plate-like transparent member is detected based on the difference information and the flare information stored in the memory.

With this constitution, as described in the above embodiment, the attached matter on the surface of the plate-like transparent member can be detected with high accuracy by eliminating most of disturbance light and flare light.

(2) In the attached matter detector according to the above (1), wherein the light-up image and the light-out images are continuously imaged.

With this constitution, as described in the above embodiment, the disturbance light whose position is changed over a short time such as a headlight of an oncoming vehicle can be preferably eliminated.

(3) In the attached matter detector according to the above (1) or (2), wherein the light-out image, the light-up image and the light-out image are continuously imaged in order, and the attached matter detector further includes the light-out image comparison device (the image analysis unit 102 in this embodiment) configured to compare the light-out image just before the light-up image as the first light-out image and the light-out image just after the light-up image such as the second light-out image, and the stop device (the image analysis unit 102 in this embodiment) configured to stop the detection of the attached matter if a change in the light-out image just after the light-up image relative to the light-out image just before the light-up image exceeds the threshold by the light-out image comparison device.

With this constitution, as described in the modified example, the detection process for attached matter can be stopped when the disturbance light is greatly changed between the light-up image and the light-out image. Therefore, the false-detection due to the disturbance light can be controlled.

(4) The attached matter detector according to any one of the above (1)-(3), wherein the optical filter 205 configured to transmit only light having a wavelength which is the same as that of the light irradiated from the light source 202*a*, 202*b* is provided between the plate-like transparent member and the imaging device.

With this constitution, the load in the image process can be reduced by eliminating only the disturbance light having a wavelength which is the same as that of the light emitted from the light sources 202*a*, 202*b*.

(5) The attached matter detector according to the above (4), wherein a part of the imaging area of the imaging device is used as the attached matter imaging area which images the attached matter such as a raindrop on the surface of the plate-like transparent member such as the windshield 105, and the optical filter 205 is provided only between the plate-like transparent member and the attached matter imaging area.

With this constitution, as described in the embodiment, the problem of the image being obtained in the area except the attached matter imaging area of the imaging device can be prevented.

(6) The vehicle equipment control apparatus as a vehicle equipment control system includes the attached matter detector configured to detect attached matter on the windshield of the vehicle, and the wiper controller such as the wiper control unit 106 configured to control the operation of the wiper which eliminates the attached matter on the surface of the windshield based on the detection result of the attached matter detector, wherein the attached matter detector according to the above (1)-(5) is used as the attached matter detector.

With this constitution, the false-operation of the wiper can be controlled.

(7) The vehicle equipment control apparatus according to the above (6) further includes the lamp controller such as a headlamp controller unit 103 configured to control the irradiation direction of the headlamp or the emission intensity of the headlamp based on the image of the area anterior to the vehicle imaged by the imaging device and/or the vehicle traveling controller such as the vehicle traveling control unit configured to control the traveling of the vehicle based on the image of the area anterior to the vehicle imaged by the imaging device, wherein the exposure control when imaging the area anterior to the vehicle and the exposure control when imaging the light-up image and the light-out image differ.

With this constitution, the object anterior to the vehicle, the white line or the like can be preferably imaged, and the attached matter such as a raindrop attached on the windshield 105 can be preferably imaged.

(8) The vehicle equipment control apparatus according to the above (7), wherein the exposure control when imaging the area anterior to the vehicle is the automatic exposure control which stops the exposure if the brightness value of a predetermined portion of the image becomes a predetermined brightness value, and the exposure control when imaging the light-up image and the light-out image is controlled such that the exposure time when imaging the light-up image and the exposure time when imaging the light-out image become the same.

With this constitution, the object anterior to the vehicle, the white line or the like can be preferably imaged. The brightness value of the disturbance light in the light-up image and the brightness value of the disturbance light in the light-out image can be set to approximately the same value. Most of the disturbance light can be eliminated when generating the difference image; thus, the attached matter such as a raindrop can be detected with high accuracy.

(9) The vehicle equipment control apparatus according to the above (6) further includes the lamp controller such as the headlamp control unit 103 configured to control the irradiation direction of the headlamp and the emission intensity of the headlamp based on the image of the area anterior to the vehicle imaged by the imaging device and/or the vehicle traveling controller such as the vehicle traveling control unit configured to control the traveling of the vehicle based on the image of the area anterior to the vehicle imaged by the imaging device, wherein the image of the area anterior to the vehicle and the light-up image are simultaneously imaged in the same frame, and the image of the area anterior to the vehicle and the light-out image are simultaneously imaged in the same frame.

With this constitution, the detection of the raindrop and the detection of the object anterior to the vehicle and the white line can be simultaneously performed.

(10) The vehicle equipment control apparatus according to the above (9), wherein the exposure control when imaging each image is the automatic exposure control which stops the exposure if the brightness value of a predetermined portion of the image becomes a predetermined brightness value, and the difference information-obtaining device is configured to correct each image based on the exposure time when imaging each image, and obtain the difference information between the corrected light-up image and the corrected light-out image.

With this constitution, most of disturbance light can be eliminated when generating the difference image even if the exposure time when imaging the light-up image and the exposure time when imaging the light-out image differ. Therefore, the raindrop detection can be performed by the automatic exposure control; thus, the image of the area anterior to the vehicle can be imaged with high accuracy.

(11) The vehicle equipment control apparatus according to the above (9), wherein the exposure control when imaging each image is the automatic exposure control which stops the exposure if the brightness value of a predetermined portion of the image becomes a predetermined brightness value, and the attached matter detector is configured to anticipate the exposure time when imaging the light-up image, and control the irradiation light volume of the light source based on the anticipated exposure time.

With this constitution, as described in the above embodiment, the brightness value of the reflection light by the attached matter such as a raindrop can be set to be the same even if the exposure time differs. In this way, the total brightness value of the difference image between the light-up image and the light-out image can be used as the difference information, and the number of raindrops can be accurately detected when detecting a raindrop.

According to the embodiment of the present invention, the disturbance light can be eliminated by obtaining the difference information between the light-up image and the light-out image. More specifically, the light-up image becomes an image only by the disturbance light because the disturbance light only enters in the imaging device in the imaging with the turned-off light source. On the other hand, the light-up image becomes an image by both of the disturbance light and the reflection light because both of the disturbance light and the reflection light by the attached matter on the plate-like transparent member enter the imaging device in the imaging with the turned-on light source. Accordingly, the disturbance light can be eliminated by obtaining the difference information between the light-up image by both of the disturbance light and the reflection light and the light-out image only by the disturbance light. Thus, the false-detection by the disturbance light can be controlled.

By detecting the attached matter on the surface of the plate-like transparent member based on the difference information from which the disturbance light component is eliminated and the previously obtained flare information, the flare light of the noise component included in the difference information can be distinguished from the reflection light by the attached matter. The reflection light component by the attached matter can be thereby extracted from the difference information. Therefore, the attached matter having a brightness value which is the same as that of the flare light can be detected, and the detection accuracy can be improved compared to the invention described in Patent Document 2.

Although the embodiment of the present invention has been described above, the present invention is not limited thereto. It should be appreciated that variations may be made in the embodiment described by persons skilled in the art without departing from the scope of the present invention.

CROSS-REFERENCE TO
RELATED-APPLICATION

The present application is based on and claims priority from Japanese Patent Application No. 2011-241519, filed on, Nov. 2, 2011, and Japanese Patent Application No. 2012-145674, filed on Jun. 28, 2012, the disclosures of which are hereby incorporated by reference in their entirety.

The invention claimed is:

1. An attached matter detector, comprising:
a light source configured to irradiate light toward a plate-like transparent member from one surface thereof;
an imaging device configured to image reflection light by attached matter on a surface of the plate-like transparent member;
a memory configured to previously store flare information obtained by the image device by turning on the light source in a state without having disturbance light and the attached matter on the surface of the plate-like transparent member; and
a difference information-obtaining device configured to obtain difference information between a light-up image as an image obtained by the imaging device with the turned-on light source and a light-out image as an image obtained by the imaging device with the turned-off light source, wherein
the attached matter on the surface of the plate-like transparent member is detected based on the difference information and the flare information stored in the memory,
a part of an imaging area of the imaging device is used as an attached matter imaging area which images the attached matter attached to the surface of the plate-like transparent member,
the light-out image, the light-up image, and the light-out image are continuously imaged in order,
a light-out image comparison device configured to compare the light-out image just before the light-up image and the light-out image just after the light-up image, and
a stop device is configured to stop detection of the attached matter if a change in the light-out image just after the light-up image relative to the light-out image just before the light-up image exceeds a threshold by the light-out image comparison device.

2. The attached matter detector according to claim 1, wherein
the light-up image and the light-out images are continuously imaged.

3. The attached matter detector according to claim 1, wherein
an optical filter configured to transmit only light having a wavelength which is the same as that of a light irradiated from the light source is provided between the plate-like transparent member and the imaging device.

4. The attached matter detector according to claim 3, wherein a part of an imaging area of the imaging device is used as an attached matter imaging area which images the attached matter on the surface of the plate-like transparent member, and the optical filter is provided only between the plate-like transparent member and the attached matter imaging area.

5. A vehicle equipment control apparatus, comprising:

an attached matter detector configured to detect attached matter on a windshield of a vehicle; and a wiper controller configured to control an operation of a wiper which eliminates the attached matter on the surface of the windshield based on the detection result of the attached matter detector, wherein the attached matter detector according to claim 1 is used as the attached matter detector.

6. The vehicle equipment control apparatus according to claim 5, further comprising:

a lamp controller configured to control an irradiation direction of a headlamp or an emission intensity of the headlamp based on an image of an area anterior to the vehicle imaged by the imaging device; and/or a vehicle traveling controller configured to control traveling of the vehicle based on the image of the area anterior to the vehicle imaged by the imaging device, wherein an exposure control when imaging the area anterior to the vehicle and an exposure control when imaging the light-up image and the light-out image differ.

7. The vehicle equipment control apparatus according to claim 6, wherein the exposure control when imaging the area anterior to the vehicle is an automatic exposure control which stops the exposure if a brightness value of a predetermined portion of an image becomes a predetermined brightness value, and the exposure control when imaging the light-up image and the light-out image is controlled such that the exposure time when imaging the light-up image and the exposure time when imaging the light-out image become the same.

8. The vehicle equipment control apparatus according to claim 5, further comprising:

a lamp controller configured to control an irradiation direction of a headlamp and an emission intensity of the headlamp based on an image of an area anterior to the vehicle imaged by the imaging device; and/or a vehicle traveling controller configured to control traveling of the vehicle based on the image of the area anterior to the vehicle imaged by the imaging device, wherein the image of the area anterior to the vehicle and the light-up image are simultaneously imaged in the same frame, and the image of the area anterior to the vehicle and the light-out image are simultaneously imaged in the same frame.

9. The vehicle equipment control apparatus according to claim 8, wherein the exposure control when imaging each image is automatic exposure control which stops the exposure if a brightness value of a predetermined portion of an image becomes a predetermined brightness value, and the difference information-obtaining device is configured to correct each image based on the exposure time when imaging each image, and obtain difference information between the corrected light-up image and the corrected light-out image.

10. The vehicle equipment control apparatus according to claim 8, wherein the exposure control when imaging each image is an automatic exposure control which stops the exposure if a brightness value of a predetermined portion of an image becomes a predetermined brightness value, and the attached matter detector is configured to anticipate an exposure time when imaging the light-up image, and control irradiation light volume of the light source based on the anticipated exposure time.

* * * * *